United States Patent [19]

Mattes et al.

[11] Patent Number: 5,061,625

[45] Date of Patent: Oct. 29, 1991

[54] PROCESS FOR THE PREPARATION OF A MICROORGANISM WHICH FORMS α-GALACTOSIDASE BUT NOT INVERTASE, A MICROORGANISM THUS OBTAINED, AND ITS USE

[75] Inventors: Ralf Mattes, Oberhausen; Klaus Beaucamp, Tutzing, both of Fed. Rep. of Germany

[73] Assignee: Boehringer Mannheim GmbH, Mannheim, Fed. Rep. of Germany

[21] Appl. No.: 235,910

[22] Filed: Aug. 24, 1988

Related U.S. Application Data

[63] Continuation of Ser. No. 381,135, May 24, 1982, abandoned.

[30] Foreign Application Priority Data

Jun. 4, 1981 [DE] Fed. Rep. of Germany ....... 3122216

[51] Int. Cl.$^5$ .................. C12N 15/00; C12N 1/20; C12N 9/40; C12N 1/00
[52] U.S. Cl. ................ 435/172.3; 435/69.1; 435/71.1; 435/91; 435/252.33; 435/320.1; 435/100; 435/208; 435/849; 536/27; 935/14; 935/29; 935/73
[58] Field of Search .............. 435/68, 100, 172.3, 435/208, 252.33, 320, 687, 69.1, 71.1, 91, 320.1; 935/14, 29, 73; 536/27

[56] References Cited

PUBLICATIONS

Schmid et al. 1976 Eur. J. Biochem. 67, 95–104.
Freifelder D. 1983, in: *Molecular Biophy.* A Comprehensive Introduction to Prokaryotes and Eukanyotes p. 548–549.
Schmitt et al., Plasmids of Medical, Environmental and Commercial Importance (1979) p. 199 ∝ 210.
Mooi et al., Nucleic Acids Research 6 (3) (1979) p. 849–865 (1979).
Schmitt et al., Biochem. Soc. Gesellschaft Biol. Chem. 360 p. 1041 (1979).
Mattes, Biochem. Soc. Gesellschaft Biol. Chem. 359 p. 1118 (1978).

*Primary Examiner*—Elizabeth C. Weimar
*Assistant Examiner*—Christopher Low
*Attorney, Agent, or Firm*—Felfe & Lynch

[57] ABSTRACT

To prepare a microorganism producing α-galactosidase, not only a DNA containing an α-galactosidase gene but also a vector which is appropriate to the transformable cells to be used and contains antibiotic resistance genes are completely split with restriction endonuclease Sal I, the fragment of approximately four megadaltons of relative molecular weight is obtained from the fragments of the DNA containing the α-galactosidase gene, is mixed with the solution of the vector also split with Sal I, and is recombined in the presence of DNA ligase with the formation of a recombinant DNA. The recombinant DNA obtained is incubated with transformable cells with transformation of the recombinant DNA into the cells, the transformed cells are cultured on a nutrient substrate containing raffinose as sole carbon source, the antibiotic-resistant colonies formed are isolated and lysed, the plasmid DNA is isolated from the lysate, the plasmid DNA is split with restriction endonuclease Hind III or Eco R I, and the obtained solution is diluted, and treated with DNA ligase. The renatured plasmids obtained are again introduced into transformable cells, the transformed cells are again cultured on a nutrient substrate containing raffinose as carbon source as well as antibiotic, and the colonies formed which do not utilize raffinose are isolated. A micro-organism is thus obtained which does form an α-galactosidase requiring no cofactors, but which does not form invertase.

6 Claims, No Drawings

PROCESS FOR THE PREPARATION OF A MICROORGANISM WHICH FORMS α-GALACTOSIDASE BUT NOT INVERTASE, A MICROORGANISM THUS OBTAINED, AND ITS USE

This is a continuation of application Ser. No. 381,135, filed May 24, 1982.

The present invention is concerned with a process for the production of a micro-organism which produces an α-galactosidase needing no cofactors, but which does not form invertase, and it is also concerned with the use of such a micro-organism for the production of α-galactosidase, and with new micro-organisms.

In addition to the mainly-occurring sugar component saccharose, extracts of sugar beet contain small amounts of raffinose, which is a trisaccharide consisting of the monosaccharides galactose, glucose and fructose. Raffinose has the undesirable property that it concentrates in the crystallization supernatants and, when the content thereof exceeds about 1% of the total mass of the sugar, makes the crystallization thereof difficult or, in the case of some processes, even prevents crystallization. In one sugar factory alone, in the course of an approximately 3-month period, 5 to 10 tonnes of raffinose are produced daily in the crystallization supernatant. In the Federal Republic of Germany alone, the amount of raffinose produced daily is probably of the order of more than 200 tons.

The conversion of raffinose into saccharose is an important economic factor which hereto has not been dealt with at all or to only an insufficient extent because appropriate techniques having the desired degree of precision are not available. The term "precision" in this connection is to be understood to mean a selective splitting off of galactose from the raffinose molecule leaving a saccharose which cannot be further split or broken down by the agent employed. Hitherto, this has not been possible either chemically or enzymatically.

Enzymatic methods are known in which use is made of a naturally-occurring enzyme, α-galactosidase. By definition, this enzyme splits off the galactose quantitatively from the raffinose molecule. However, all α-galactosidase preparations hitherto known are always contaminated with the enzyme invertase which splits saccharose into glucose and fructose. In view of the high concentration of saccharose in comparison with the raffinose present (about 60:1 to 80:1), even a slight contamination of the α-galactosidase by invertase has a very disturbing effect because considerable amounts of saccharose are further split and all that is accomplished is the exchange of one undesirable contaminant for another. Therefore, it has scarcely been possible to make practical use of the corresponding processes.

It is to be noted in this connection that the known ogalactosidases contaminated with invertase, which have heretofore been used technically, are preponderantly fungal enzymes which, because of their availability, have found use in sugar technology. Besides the mentioned contamination, they suffer from the additional disadvantage that, as fungal enzymes, they have an activity maximum which distinctly lies in the acidic pH range, which, in the case of large-scale technology (several hundred cbm/hour per factory) gives rise to considerable problems in the case of acidification and reneutralisation.

One α-galactosidase is known which, after purification, is said to be free of invertase. However, as cofactors, this α-galactosidase requires manganese ions and NAD. Furthermore, it is not very stable and is only present in the biomass in low concentration. Therefore, this α-galactosidase has not been taken into consideration in processes carried out under conditions of a continuous sugar production.

Therefore, it is an object of the present invention to make available an α-galactosidase which, by its very nature, is absolutely free from invertase. At the same time, the enzyme is also to possess the following properties: it is to manifest its highest activity in the region of the neutral pH point, it should have a reasonable temperature stability, it should be able to maintain its activity for a comparatively long period of time in relatively concentrated sugar solutions or in concentrations of plant extracts (sugar beet) and it should not require any cofactors.

In order to solve this problem, the present invention starts from the view that by using a new DNA combination it ought to be possible to: (i) irreversibly remove the enzyme invertase, which is usually associated with α-galactosidase, by deleting the gene fragment coding for invertase, and (ii) to amplify, in a vector, the gene fragment coding for α-galactosidase. As a result of an effect achieved by high gene dosage and by altering gene regulation, it is possible to obtain the desired enzyme (α-galactosidase) in a high concentration and free of invertase. Ideally, it ought to be possible to use the bacterial extract itself, or in an as-good-as immobilized form. A prerequisite for this would be the discovery of an appropriate process, an appropriate operon, and appropriate restriction endonucleases.

This object is achieved in accordance with the invention by a process for the preparation of a micro-organism which [produces an] α-galactosidase not requiring the cofactors nor forming invertase, this process being characterized by the fact that [1] a DNA containing an α-galactosidase gene and [2] a vector appropriate to the transformable cells that are to be used are completely split with restriction endonuclease Sal I (EC 3.1.23.37), a fragment is obtained from the fragments of the DNA containing the α-galactos[idas]e gene, which fragment has a relative molecular weight of about 4 megadaltons, this fragment is mixed with a solution of the vector also split with Sal 1, and recombined in the presence of DNA ligase with the formation of a recombinant DNA, the recombinant DNA obtained is incubated with transformable cells, the transformed cells are cultured on a nutrient substrate containing raffinose as the sole source of carbon, the antibiotic-resistant colonies formed are isolated and lysed, the plasmid DNA is isolated from the lysate, this plasmid DNA is split with restriction endonuclease Hind III (EC 3.1.23.21) or Eco RI (EC 3.1.23.13), the solution obtained is diluted and treated with DNA ligase, the renatured plasmids obtained are again introduced into transformable cells, the transformed cells are again cultured on a nutrient substrate containing raffinose as carbon source as well as antibiotic, and the colonies formed which do not utilise raffinose are isolated.

One DNA containing the α-galactosidase gene is preferably obtained from *E. coli* BMTU 2743, DSM 2092 by culturing it in an appropriate nutrient medium at an elevated temperature, preferably at 37° to 42° C., precipitating with polyethylene glycol and purifying, for example by density gradients and phenol extraction.

The splitting not only of the DNA containing the α-galactosidase gene but also of the vector DNA takes place in a known manner by the action of restriction endonuclease Sal I, preferably at a temperature of from 35° to 37° C., until the DNA molecules are completely split. The endonuclease is subsequently denatured, preferably by heating. The fragments obtained of the DNA containing the α-galactosidase gene are fractionated by gel electrophoresis and the fragment With a relative molecular weight of about 4 megadaltons is isolated.

The recombination of this fragment with the split vector takes place by simple mixing of the solution and the addition of an appropriate DNA ligase, DNA ligase of the T4 phages (EC 6.5.1.1) being preferably used but DNA ligases of other origins can also be used.

The recombinant DNA is thus obtained and it is mixed in the usual way with transformable cells (so-called competent strains which display the ability to take up DNA), the transformation reaction thereby taking place.

As transformable cells there can be used, within the scope of the present invention, those cells known for this purpose. Examples of appropriate transformable cells include *E. coli, Klebsiella pneumoniae, Pseudomonas aeruginosa, Pseudomonas putida, Saccharomvces cerevisiae* and *Bacillus subtilis*. *E. coli* are especially preferred, for example the strain BMTU 2744, DSM 2093.

This applies especially for the first transformation step within the scope of the process according to the present invention. For the second transformation step in the process according to the present invention, the choice of the transformable cells is made having regard to the other properties of these cells such as the usefulness of the cell components after obtaining the α-galactosidase, growth properties and availability. For the second transformation, *E-coli* and *Pseudomonas putida* are again especially preferred.

The choice of the vector depends upon the choice of the transformable cells. In the case of using *E. coli* strains as the transformable cells, the plasmid pBR 322 (DSM 2089) is preferably used as vector, this being commercially available (see Nucl. Acid Res., 5, 2721-2728/1978).

For Saccharomyces cells, as vector there can be used, for example, the plasmid p.FL 1, described by Mercereau-Puijalon et al. (Gene, 11, 163-167/1980). For *Bacillus subtilis* cells, there is especially preferred as vector the plasmid pHV 23, described by B. Michel et al. (Gene, 12, 147-154/1980). For all the other above-mentioned micro-organisms, as well as for *E. coli*, pRSF 1010 is also suitable. The same applies analogously for pKT 230 (both described in "Microbial Degradation of Xenobiotics and Recalcitrant Compounds", ed. Hütter and Leisinger, pub. Acad. Press, London, 1981).

Of the transformable cells which are to be considered, those are preferred which themselves do not contain plasmids, for example the above-mentioned *E. coli* BMTU 2744, DSM 2093.

The use of a DNA containing the α-galactosidase gene is important for the present invention, as well as the splitting first with Sal I and the splitting with Hind III or Eco RI of the plasmid DNA obtained after the first transformation since these restriction endonucleases bring about a splitting at the point of the DNA which is critical for the present invention. For the recombination of the 4 megadalton fragment with the split vector there can, in principle, be used any appropriate DNA ligase, the DNA ligase of the phage T4 being preferred. The religation takes place by simple mixing of the solutions in question in the presence of ATP, of a sulphhydryl compound and of magnesium ions.

In order, after the religation, to find those cells which contain the vector containing the α-galactosidase gene, culturing takes place on a minimal medium which contains raffinose as the sole source of carbon, as well as the necessary salts. Because of the use of a vector containing antibiotic-resistance genes, there is preferably also added to the medium an antibiotic against which the genes contained in the vector mediate resistance. For Example, the plasmid pBR 322 contains resistance genes against ampicillin and tetracycline so that, in this case, one of these antibiotics is preferably used, which suppresses the growth of those cells which, after the transformation, do not contain this gene. By a minimal medium, there is here to be understood one which, apart from the necessary salts, only contains raffinose.

The splitting of the hereby obtained hybrid plasmid DNA with Hind III or Eco RI brings about the deletion of the gene sequence coding for the expression of raffinose permease and invertase. Therefore, in the case of renaturing by the action of DNA ligase, vectors are obtained which no longer contain those genes which are undesired in the intended process and which are used for the transformation of the second stage for which otherwise the statements made above regarding the transformation of the stage apply in the same way.

The cells obtained in the second transformation step are selected by culturing them on a complete nutrient substrate with pH indicator which contains raffinose as carbon source and the appropriate antibiotic. Complete nutrient substrates contain peptone and yeast extract in addition to the components of the minimal nutrient substrate. Those transformed cells in which the genes for a raffinose permease and invertase are no longer present as a result of the deletion can no longer transport raffinose into the cells and thus cannot utilise it. The pH of the medium thereby remains in the neutral range which, in turn, does not result in a colour change. Therefore, they can be differentiated from and separated from cells in which these gene sequences have not been deleted and which take up raffinose and subsequently ferment it, with the formation of acids, on the basis of the different coloration of the medium (pH indicator).

Since the cells which are not longer able directly to utilise raffinose under the influence of raffinose permease continue to form α-galactosidase which splits raffinose, but colonies of the cells which no longer utilize raffinose are also formed,[*] the differentiation between the cells which do and do not have gene sequences for raffinose permease and invertase is preferably performed by the use of MacConkey plates (obtainable from Difco and containing neutral red pH indicator) since raffinose-utilizing colonies produce a red coloration thereon, whereas colonies which do not utilize raffinose remain white. The white colonies are isolated and can then be cultured by the methods commonly employed for the micro-organism initially used.

[* original has full stop - Tr.]

We have found that the new micro-organisms can also be cultured on a large scale and remain stable. The micro-organisms yield enzyme activities which are several powers of ten greater than the enzyme activities of the initial strains.

The enzyme formed is free from traces of invertase and can split raffinose present in saccharose crystallization supernatants at about neutral pH values at technically practicable temperatures. The enzyme does not require any cofactors, such as manganese ions and NAD, has proved to be stable, and can be fixed onto carriers by conventional methods, for example by action on cyanogen bromide-activated insoluble polysaccharides. Instead of the isolated enzyme, the micro-organism itself can also be fixed onto appropriate carriers and used technically in this form. In this way, the cell membranes which have become impermeable to raffinose as a result of the permease gene deletion, again become permeable to raffinose due to the fixing procedure. In this case, all the conventional fixing methods can be used.

The isolation of the α-galactosidase from the new micro-organisms can take place in the manner usual for obtaining α-galactosidase. One preferred process is the digestion of the biomass by conventional methods, such as high pressure dispersion, ultrasonic treatment and the like. It is preferable to use digestion methods which are suitable for the original micro-organism.

After the digestion, a polyanion precipitation is preferably carried out in which the α-galactosidase usually remains in the supernatant. Preferred polyanions include the polyethyleneimines and especially those of medium molecular weight.

The enzyme can be precipitated from the supernatant, thus obtained by precipitation with ammonium sulphate, the fraction obtained with 0.8 to 1.6M ammonium sulphate preferably being obtained. By means of dialysis and lyophilisation, there is obtained a high yield of α-galactosidase which has a purity of more than 90% and is suitable for technical use.

By the use of plasmid pBR 322 as vector and of E. coli BMTU 2744, DSM 2093 as transformable cells, by means of the above-described process there is obtained the new micro-organism E. coli BMTU 2742, DSM 2091, which is also a feature of the present invention. This new micro-organism is characterised by the following properties:

It contains the plasmid pBT 102, is resistant to 50 μg./ml. of ampicillin and constitutively produces intracellularly α-galactosidase which does not require any cofactors but does not produce invertase. Otherwise, it does not differ from the E. coli K-12 strain and can be cultured at 37° C. in a standard medium, preferably with aeration.

New micro-organisms obtained by the process according to the present invention, which are characterised by a high content of α-galactosidase with the abovementioned especially advantageous properties (up to 30% of the total amount of soluble protein can consist of α-galactosidase), are able to transmit their new properties to other micro-organisms. The micro-organisms thus obtained are also the sub3ect matter of the present invention.

One possibility for transmission is, for example, a mutual culturing of a micro-organism obtained by the process according to the present invention with a receptor micro-organism, for example by incubation on agar. If, for example, for the second transformation stage of the process according to the present invention, use is made of an E. coli strain which contains the plasmid RP 4 (cf. J. Bacteriol., 108, 1244–1249/1971), then a micro-organism is formed which, in addition to RP 4, also contains the hybrid vector, such as pBT 103 (i.e. contains two plasmids). By mutual culturing with Pseudomonas strains, this micro-organism readily transfers pBT 103 thereto.

The particular transformable forms of the microorganism used for the process, i.e. the so-called competent strain, are obtained in the manner known to the expert. The culturing preferably takes place up to the end of the exponential growth phase. The cells are then isolated and suspended in an ice-cooled solution of calcium chloride. In this form, they are capable of taking up DNA.

In the case of using E. coli, the medium used for the culturing is preferably the so-called Standard II nutrient broth of the firm Merck, Darmstadt.

Thus, the present invention provides a process for the production of micro-organisms which form the enzyme α-galactosidase with a very high activity without, at the same time, producing invertase. In this may, a source is provided for α-galactosidase which is far better suited for the splitting of raffinose o of other α-galactosidically-linked sugars, for example in the case of sugar crystallisation from beet sugar, than the previously known α-galactosidase preparations. In this way, it is possible economically to solve on a large scale the problem of raffinose concentration in the production of sugar from sugar beet. However, the micro-organism according to the present invention and the impure or purified α-galactosidase preparations obtained therefrom can also be used for other purposes in foodstuff technology in which a splitting of α-galactosidic carbohydrates is desired. One example of this is the removal of stachyose from soya meal. This removal is necessary if the soya meal is to be used for foodstuff purposes.

The following Examples are given for the purpose of illustrating the present invention

EXAMPLE 1

From the *Escherichia coli* strain BMTU 2743, DSM 2092 containing DNA with P1 raf as α-galactosidase gene, there are produced new strains with a high degree of productivity for α-galactosidase by means of the following process steps:

(1) Production of P1 raf DNA, which carries the genetic information for the raf operon, from a P1 raf lysate.

The strain *Escherichia coli* BMTU 2743 (thr−, leu−, thi−, lac Y, ton A, raf+, Plts lysogen), which is derived from E. coli K-12, BMTU 2744, DSM 2093, is cultured for 4 hours at 30° C., while shaking, in 1 litre of nutrient broth which contains, by weight, 1% trypton, 0.5% yeast extract, 0.2% glucose and 0.5% sodium chloride and has been adjusted to a pH value of 7.8, and, upon reaching an optical density of 0.5 $OD_{650}$ (measured at 650 nm), is further shake cultured for 2 hours at 40° C. for the heat induction of the temperature-sensitive phage repressor. The liberated phages are obtained from the medium supernatant by precipitation with polyethylene glycol and purified by means of cesium chloride density gradients. After phenol extraction and dialysis against a buffer (10 mM tris ..HCl, pH 8.0), there is obtained 0.6 mg. of purified phage DNA.

(2) Production of the vector DNA.

For cloning the fragments of the P1 raf DNA, there is used DNA of the plasmid pBR 322, a vector which contains not only ampicillin- resistance genes but also tetracycline-resistance genes as marker genes. Use can be made either of commercially-available plasmid or of plasmid produced in the following way:

An *Escherichia coli* strain which contains the plasmid pBR 322 is shake cultured at 37° C. in 1 litre of nutrient broth of the same composition as that used above in (1) up to the end of the exponential growth phase. Then, after the addition of 150 μg./ml. of chloramphenicol, the culture is further shaken for 15 hours at the same temperature. With the help of this process, the plasmid DNA is preferentially multiplied and enriched in the bacteria. The bacterial cells are ionic detergent and the lysate centrifuged for 30 minutes at 48000 g in order to obtain the supernatant liquid. 420 μg. of the plasmid DNA is then obtained therefrom with the help of two cesium chloride-ethidium bromide equilibrium density gradient centrifugations, subsequent phenol extraction and dialysis against a buffer (10 mM tris HCl, pH 8.0).

(3) Insertion of the raf operon from Pl raf into the vector.

10 μg. each of the Pl raf DNA and of the vector DNA are treated at 37° C. for 1 hour with restriction endonuclease Sal I in order completely to split the DNA molecules and then, in each case, heated to 65° C. for 5 minutes.

The Pl raf DNA is thereafter fractionated in a 0.7% agarose gel by electrophoresis. The fragment with the relative molecular weight of 4 megadaltons is cut out and, after phenol extraction and dialysis in a buffer (10 mM tris HCl, pH 8.0), is obtained in a solution.

The solution of the so-obtained fragment of the Pl raf DNA is mixed with the solution of the split pBR 322 vector DNA and, with the addition of ATP, dithioerythritol and maqnesium chIoride, is subjected for 24 hours at 4° C. to the action of DNA ligase of the phage T4. The solution thus obtained contains the recombinant DNA.

(4) Genetic transformation of *E. coli* bacteria with recombinant DNA which contains the genetic information for α-galactosidase.

A normal *E. coli* strain (BMTU 2744, DSM 2093) is shake cultured in 50 ml. nutrient broth at 37° C. up to the end of the exponential growth phase. The cells are collected and suspended in a 50 mM calcium chloride solution in an ice bath.

This suspension is mixed with the solution of the recombinant DNA from stage 3) and kept for 20 minutes in an ice bath and then warmed to 37° C. for 3 minutes. The cells are inoculated over into nutrient broth and shaken for 45 minutes at 37° C., the transformation reaction thereby being completed. The cells are collected, washed and resuspended. A small amount of the cell suspension is coated on to an agar plate which, per litre, contains 10.5 g. dipotassium hydrogen phosphate, 4.5 g. monopotassium dihydrogen phosphate, 1 g. ammonium sulphate, 0.5 g. sodium citrate dihydrate, 0.1 g. magnesium sulphate heptahydrate, 1 mg. thiamine, 2 g. raffinose, 25 mg. ampicillin and 15 g. agar, the pH value being adjusted to 7.2. The plate is kept at 37° C. After 2 days, numerous colonies appear on the plate. All the colonies are removed, purified and isolated.

Each of the colonies so obtained has the ability to utilise raffinose as the sole source of carbon and, at the same time, is ampicillin-resistant. Thus, it has properties which are different from those of the strain of the host organism used. This means that only the cells of the growing colonies are selected which contain the pBR 322 plasmid in which the Sal I fragment from Pl raf has been inserted with the α-galactosidase gene.

From the colonies obtained, there.is, in each case, isolated the plasmid DNA by the process described above in (2). The plasmids from all of the colonies display, after treatment with restriction endonuclease Eco RI or Hind III and analysis by electrophoresis on agarose gels, two fragments which, depending upon the originating colony of the hybrid plasmid, can be assigned to two different classes of magnitude but which, in totality, are equal.

Both classes of magnitude are found in the approximate ratio of 1:1. The different analysis results for both classes of fragment magnitude are to be attributed to the different integration direction of, the Sal I fragment from Pl raf into pBR 322.

For further working up, a plasmid of a colony is selected which, after treatment with restriction enzyme Eco RI or Hind III, gives a smaller second fragment than the plasmids of other colonies. This plasmid is called pBT 100 (BMTU 2741) (DSM 2090). Bacteria which carry this plasmid can use raffinose as the sole source of carbon and constitutively produce all enzymes of the raf operon.

(5) 10 μg. amounts of the plasmid pBT 100 from BMTU 2741 (DSM 2090) are treated either with the restriction endonuclease Hind III or with the restriction endonuclease Eco RI at 37° C. for 1 hour in order to split the DNA molecules. This is followed by heating for 5 minutes to 65° C.

The plasmid DNA solutions treated in this manner are diluted and, in each case, subjected to a renaturing treatment with T4 ligase in the. manner described above under 3).

Subsequently, in the manner described above under (4), competent cells of the *E. coli* strain are, in each case, introduced into solutions of the renatured DNA from the last stage of the transformation reaction. A small amount of each of the cells treated in this manner is coated on to a MacConkey raffinose plate (Difco Laboratories, Detroit) with 25 μg./ml. ampicillin. On the plate from the transformation with plasmid DNA previously treated with Hind III, there can be seen about 20 colonies after incubation at 37° C. for 24 hours and on the plate from the transformation of DNA previously treated with Eco RI there are found, under the same conditions, about 30 colonies. The ratio of red to white colonies is 1:4 in the first case and 1:3 in the second case.

The red colonies are, in each case, capable of breaking down raffinose and thus still contain the whole raf operon, whereas none of the white cells are capable of breaking down raffinose. However, these still constitutively produce the enzyme α-galactosidase, as is demonstrated by a test in the cell-free extract with p-nitrophenyl-α-galactoside (α-PNPG) when the cells are previously cultured without the addition of raffinose in nutrient broth at 37° C. up to the stationary phase Therefore, these cells possess properties which differ from those of the host organism and of the cells BMTU 2741 (DSM 2090) which are transformed with pBT 100.

The plasmid which is obtained after previous Hind III treatment of pBT 100 in the white colonies on the MacConkey plates is called pBT 101 and that after the previous Eco RI reaction is called pBT 102. The *E. coli* strain with pBT 102 is called BMTU 2742 (DSM 2091).

(6) Obtaining α-galactosidase from strains with pBT 102 (BMTU 2742).

The following Table 1 shows the experimental results of testing the cell-free extracts for a content , . of α-galactosidase with α-PNPG at 25° C. after culturing of the strain BMTU 2742, which represents one of the clones obtained in stage (5). The cells are inoculated into 10 ml. of the nutrient broth in a 100 ml. flask and shaken for 15 hours at 37° C. Control experiments were carried out by culturing the original strain BMTU 2743 under the same conditions but with the addition of 0.2% raffinose to the medium.

As can be seen from the following Table 1, the extracts of the strain BMTU 2742 display a remarkably increased content of α-galactosidase in comparison with BMTU 2743.

TABLE 1

| Strain No. | α-Galactosidase U/mg.* |
|---|---|
| BMTU 2742 (DSM 2091) | 10 |
| BMTU 2743 (DSM 2092) | 0.4 |

*mg. of soluble protein in the crude extract.

Under these test conditions, in the known strain *E. coli* BMTU 2744 there is to be found an activity of <0.001 U/mg.

EXAMPLE 2

In the manner described in Example 1 (1), from *E. coli* BMTU 2481 (DSM 2101) phages are isolated and split with Eco R I in the manner described in Example 1(3). The preparation so obtained serves as a source for DNA which contains the genetic information for α-galactosidase.

For the production of the vector DNA, from *E. coli* BMTU 2745 (DSM 2100) there is obtained DNA of the plasmid pKT 230 in the manner described in Example 1(2), except that culturing of the cells takes place overnight at 37° C. with aeration in a nutrient broth to which chloramphenicol has not been added.

The plasmid DNA obtained is split with Eco R I in the manner described in Example 1(3).

The isolation of the phage fragment of the order of magnitude of 4 megadaltons and the ligation of this fragment with split pKT 230 DNA also takes place in the manner described in Example 1(3).

The so obtained solution of the recombinant DNA is transformed in *E. coli* BMTU 2602 (DSM 2102) in the manner described in Example 1(4). Selection takes place on an agar plate which contains 25 μg./ml. of kanamycin. There are obtained about 40 colonies which are resistant to kanamycin and which are tested for streptomycin sensitivity (50 μg./ml.). About 20 streptomycin-sensitive colonies are found which are, however, still resistant to 20 μg. of streptomycin. The formation of α-galactosidase is demonstrated in the isolated colonies in the manner described in Example 1. The new strain *E. coli* BMTU 2746 (DSM 2103) , . differs from the original strain BMTU 2602 (DSM 2102) by its kanamycin resistance, its low streptomycin resistance and its α-galactosidase production but otherwise corresponds to the original strain. The cells of this new strain contain.the plasmid pBT 103, which contains the α-galactosidase gene as is demonstrated by the detection of the α-galactosidase formed.

For the transfer of pBT 103 from BMTU 2746 (DSM 2103) to *Pseudomonas putida* BMTU 2749 (DSM 2106), there are first mixed cells of bacteria of the strain BMTU 2746 (DSM 2103) and BMTU 2747 (DSM 2104) growing in the logarithmic phase, the latter strain containing the transferable plasmid RP 4, and plated on to a Standard II agar plate (Merck, Darmstadt) containing up to 20 αg./ml. of streptomycin and 20 αg./ml. of tetracycline. After incubation at 37° C. , about 50 colonies grow. One colony is isolated. By coating on to plates with appropriate antibiotic content, it is demonstrated that this new strain BMTU 2748 (DSM 2105) is resistant to 20 μg./ml. of streptomycin, 26 μg./ml. of kanamycin, 20 μg./ml. of tetracycline and 50 μg./ml. of ampicillin. The said strain contains the plasmids RP 4 and pBT 103, which is demonstrated by the detection of the α-galactosidase formed.

The transfer of the plasmid pBT 103 from BMTU 2748 (DSM 2105) to *Pseudomonas putida* BMTU 2749 (DSM 2106) takes place by mixing cultures of both strains growing in th logarithmic phase and incubation of the mixture on a Standard II agar plate (Merck, Darmstadt) at 30° C. for 24 hours, subsequent floating off of the cells into sterile nutrient broth and plating o to agar plates with selective nutrient broth Standard II which contains 100 μg./ml. of kanamycin and 25 μg./ml. of chloramphenicol. After 2 days, about 20 colonies grow which are purified and which are identified as being tetracycline-sensitive and as being *Pseudomonas putida* with the plasmid pBT 103 which contains the α-galactosidase gene (BMTU 2750; DSM 2107). The α-galactosidase detection takes place in the manner described in Example 1.

EXAMPLE 3

Splitting of raffinose in the crystallisation run-off of a sugar factory.

45 ml. of run-off, which cgntained 802 mg. of raffinose, were diluted with 45 ml. of water. The solution was adjusted to a pH value of 6.5. In parallel experiments, this solution was incubated not only with a cell-free extract but also with toluene-treated cells of the strain *E. coli* DSM 2091 according to the present invention, the extract and the treated cells each containing 57 U of α-galactosidase.

The mixture was left to stand at 40° C. for 60, 120 and 180 minutes. At the given times, the galactose content of the solution was determined by means of an enzymatic test and the residual amount of raffinose in the batch was calculated. After the stated treatment times, there was found a residual amount of raffinose of 459, 378 and 315 mg., corresponding to a reduction of the original raffinose content of 57.2%, 47.1% and 39.2%. The results obtained are summarized in the following Table 2.

TABLE 2

| 90 ml. of crystallisation run-off solution containing 802 mg. of raffinose, treated with 57 U α-galactosidase at 40° C. and pH 6.5 | | |
|---|---|---|
| treatment time (minutes) | raffinose content (mg.) | % of initial value |
| 0 | 802 | 100.0 |
| 60 | 459 | 57.2 |
| 120 | 378 | 47.1 |
| 180 | 315 | 39.2 |

We claim:
1. Process for the preparation of a stable *E. coli* which constitutively produces at least 10 U of alpha galactosidase per mg of cell free extract wherein said alpha galactosidase splits raffinose at about neutral pH without requiring cofactors or inductors, and comprising:
(i) cleaving a DNA containing an alpha-galactosidase gene with SalI to form a DNA fragment which has a relative molecular weight of about 4 megadaltons and contains said alpha galactosidase gene;

(ii) cleaving a vector appropriate to a first transformable *E. coli* which contains a predetermined antibiotic resistance gene with SalI, to form DNA fragments of said vector;

(iii) mixing said DNA encoding alpha-galactosidase with a solution of vector DNA fragments;

(iv) recombining the DNA encoding alpha galactosidase and vector fragments in the presence of DNA ligase to form a recombinant DNA plasmid;

(v) incubating said plasmid with said first transformable *E. coli* to obtain transformed cells;

(vi) culturing the transformed cells on a nutrient substrate containing raffinose as the sole source of carbon;

(vii) contacting the transformed cells with a predetermined antibiotic;

(viii) isolating colonies resistant to said antibiotic;

(ix) lysing said antibiotic resistant colonies to form a lysate;

(x) isolating plasmid DNA from the lysate;

(xi) cleaving the plasmid DNA with restriction endonuclease Hind III or EcoRI to delete genese expressing permease and ivnertase but not alpha galactosidase from said plasmid;

(xii) diluting and treating the split plasmid DNA with DNa ligase to obtain a renatured plasmid;

(xiii) introducing the renatured plasmid into a second transformable *E. coli* to obtain a second plasmid transformed cell which produces at least 10 U of alpha galactosidase per mg of cell free extract; and (xiv) isolating a biologically pure culture of cells from step (xiii) which does not utilize raffinose but which constitutively produces at least 10 U of alpha galactosidase per mg of cell free extract.

2. Process of claim 1, wherein said alpha-galactosidase gene is derived from *E. coli* DSM 2091.

3. Process of claim 1, wherein said vector containing a predetermined antibiotic resistant gene is pBR322.

4. A purified culture *E. coli* which constitutively produces at least 10 U of alpha-galactosidase per mg of cell free extract, wherein said alpha-galactosidase splits raffinose at about neutral pH values, does not require cofactors or inducers and does do not produce invertase or permease specific to alpha-galactosidase.

5. *E. coli* DSM 2091.

6. *E. coli* of claim 4, wherein said bacteria constitutively produce said alpha galactosidase at a temperature of 25° C.

* * * * *